US00PP30703P3

(12) United States Plant Patent
Nicolaï

(10) Patent No.: US PP30,703 P3
(45) Date of Patent: Jul. 16, 2019

(54) APPLE TREE NAMED 'ZOUK 32'

(50) Latin Name: *Malus domestica*
Varietal Denomination: ZOUK 32

(71) Applicant: Zouk B.V.B.A., Sint-Truiden (BE)

(72) Inventor: Johan Nicolaï, Sint-Truiden (BE)

(73) Assignee: Zouk B.V.B.A., Sint-Truiden (BE)

( * ) Notice: Subject to any disclaimer, the term of this patent is extended or adjusted under 35 U.S.C. 154(b) by 0 days.

(21) Appl. No.: 15/732,497

(22) Filed: Nov. 20, 2017

(65) Prior Publication Data

US 2019/0159376 P1 May 23, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

(56) References Cited

U.S. PATENT DOCUMENTS

PP4,121 P 10/1977 ten Hove
PP6,450 P 12/1988 Visser
PP6,955 P 8/1989 Kiddle
PP16,559 P3 5/2006 Nicolai
PP17,201 P3 11/2006 Nicolai
PP25,671 P3 7/2015 Kellerhals
2004/0025211 P1 2/2004 Zulch

OTHER PUBLICATIONS

U.S. Appl. No. 15/732,499, "Apple Tree Named 'Zouk 31'," filed Nov. 20, 2017, for inventor Johan Nicolai and for applicant Zouk B.V.B.A.
U.S. Appl. No. 15/732,496, "Apple Tree Named 'Zouk 16'," filed Nov. 20, 2017, for inventor Johan Nicolai and for applicant Zouk B.V.B.A.
U.S. Appl. No. 15/732,502, "Apple Tree Named 'Zouk G1'," filed Nov. 20, 2017, for inventor Johan Nicolai and for applicant Zouk B.V.B.A.
Fresh Plaza (2016). "Johan Nicolai presents new early Gala variety," retrieved on Oct. 16, 2018, retrieved from the Internet at http://www.freshplaza.com/article/2153468/johan-nicolai-presents-new-early-gala-variety/, 2 pp.
Guerra (2017). "Strains improve standard varieties translated and edited by Julia Strobl," European Fruit Network Jun. 2017, retrieved on Oct. 22, 2018, retrieved from the Internet at http://kp.eufrin.eu/fileadmin/user_upload/documents/804-14df1cca1323ccb72d8b027c37356dfd.pdf, pp. 14-17.
Horticulture Week (2015). "Apple varieties found by chance unveiled at show," retrieved on Oct. 22, 2018, retrieved from the Internet at https://www.hortweek.com/apple-varieties-found-chance-unveiled-show/fresh-produce/article/1370357, 2 pp.

*Primary Examiner* — Keith O. Robinson
(74) *Attorney, Agent, or Firm* — Morrison & Foerster LLP

(57) ABSTRACT

A new and distinctive variety of a *Malus domestica* apple tree, named 'ZOUK 32' that is distinguished by its medium-sized, well feathered tree that is high yielding and is tolerant to apple scab caused by *Venturia inaequalis*, is disclosed.

3 Drawing Sheets

Latin name:
Botanical classification: *Malus domestica.*
Varietal denomination: The varietal denomination of the claimed apple tree variety is 'ZOUK 32'.

BACKGROUND OF THE INVENTION

Apples are an economically important crop. Accordingly, there exists a need to develop new varieties of apple tree with improved characteristics, such as disease resistance.

BRIEF SUMMARY OF THE INVENTION

In order to meet these needs, the present invention is directed to an improved variety of apple tree. In particular, the invention relates to a new and distinct variety of apple tree (*Malus domestica*), which has been denominated as 'ZOUK 32'.

Apple tree variety 'ZOUK 32' was discovered in Sint-Truiden, Belgium as a hybrid from a controlled pollination cross of seed parent 'Rubinstep' (unpatented) and pollen parent 'Nicoter' (U.S. Plant Pat. No. 17,201). The original seedling of the new variety was first asexually propagated by T-budding and bench grafting onto 'M9 T337' (also known as 'M9 NAKBT337' or 'M9'; unpatented) rootstock, 'MM106' (also known as 'Malling-Merton 106'; unpatented) rootstock, and 'MM111' (also known as 'Malling-Merton 111'; unpatented) rootstock in 2013 and subsequently planted in a nursery bed for tree production.

The original 'ZOUK 32' tree and its progeny have been observed growing in a plot located in Gorsem, Belgium. The new variety produces fruit that matures for commercial harvesting approximately at the end of September in the Haspengouw area in Belgium.

The 'ZOUK 32' apple tree variety is distinguished from other apple tree varieties by the following unique combination of characteristics: the new variety is a medium-sized, well feathered tree that is high yielding and is tolerant to apple scab caused by *Venturia inaequalis.*

Asexual reproduction of the 'ZOUK 32' apple tree variety by T-budding and bench grafting onto 'M9 T337', 'MM106' and 'MM111' rootstocks in Sint-Truiden, Belgium shows that the foregoing and all other characteristics and distinctions are true to type and are established and transmitted through succeeding asexual propagations.

BRIEF DESCRIPTION OF THE DRAWINGS

The 'ZOUK 32' apple tree variety is illustrated by the accompanying photographs which show fruit of the tree, as well as the flowers. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are four years old.

DETAILED BOTANICAL DESCRIPTION

Figure 1:
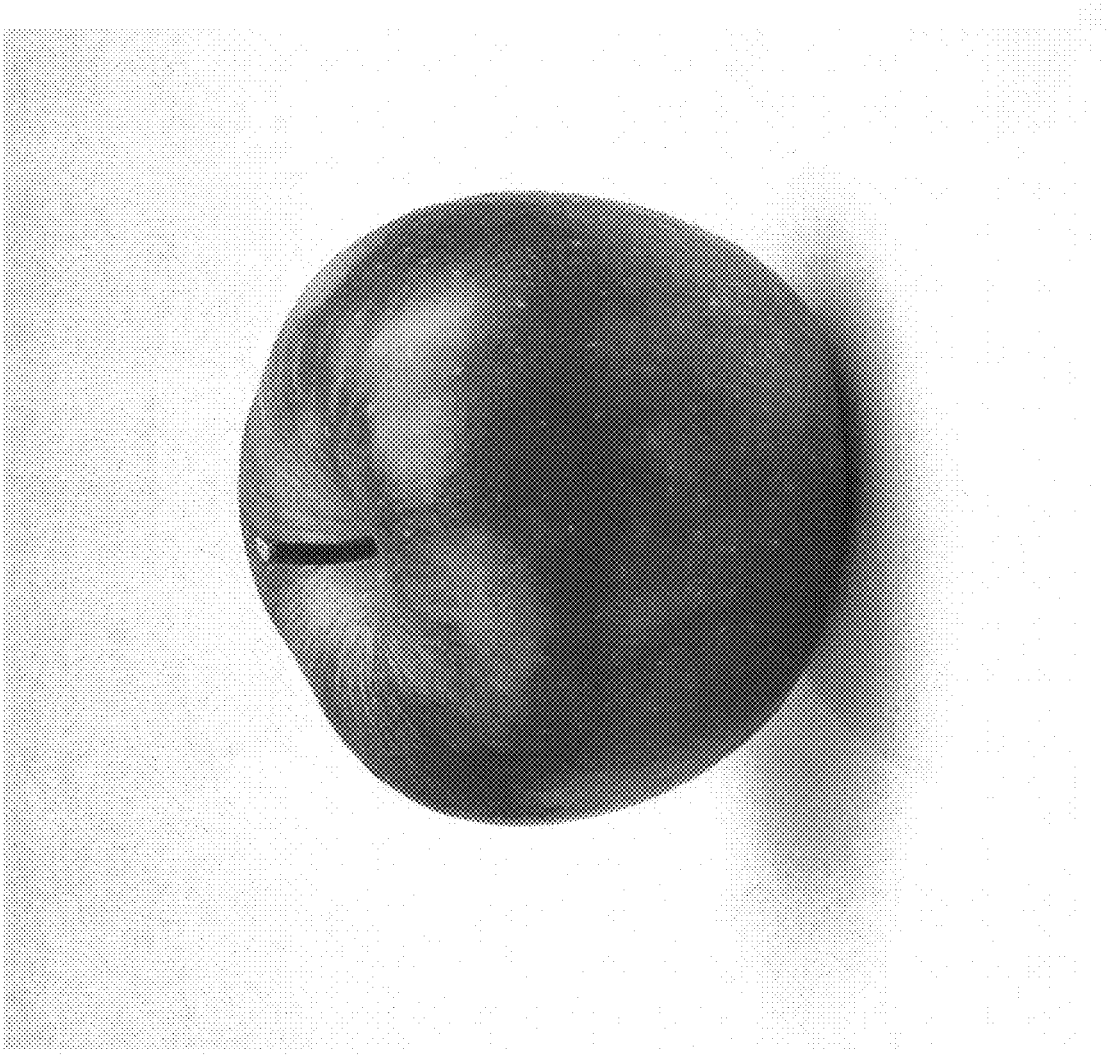
FIG. 1 illustrates fruit of apple tree variety 'ZOUK 32'.
Figure 2:
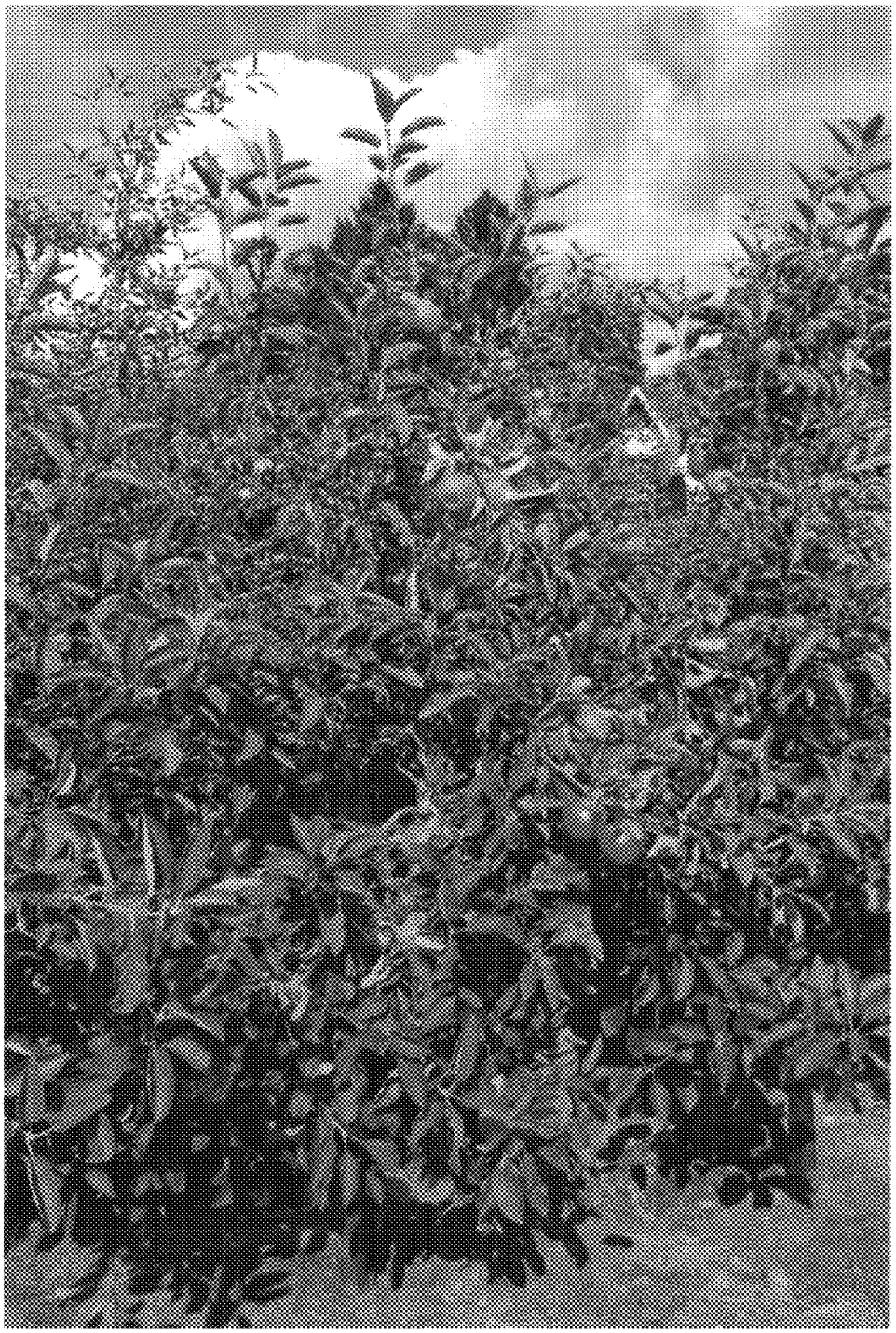
FIG. 2 illustrates a tree of apple tree variety 'ZOUK 32' with fruit on the tree (colored side).
Figure 3:
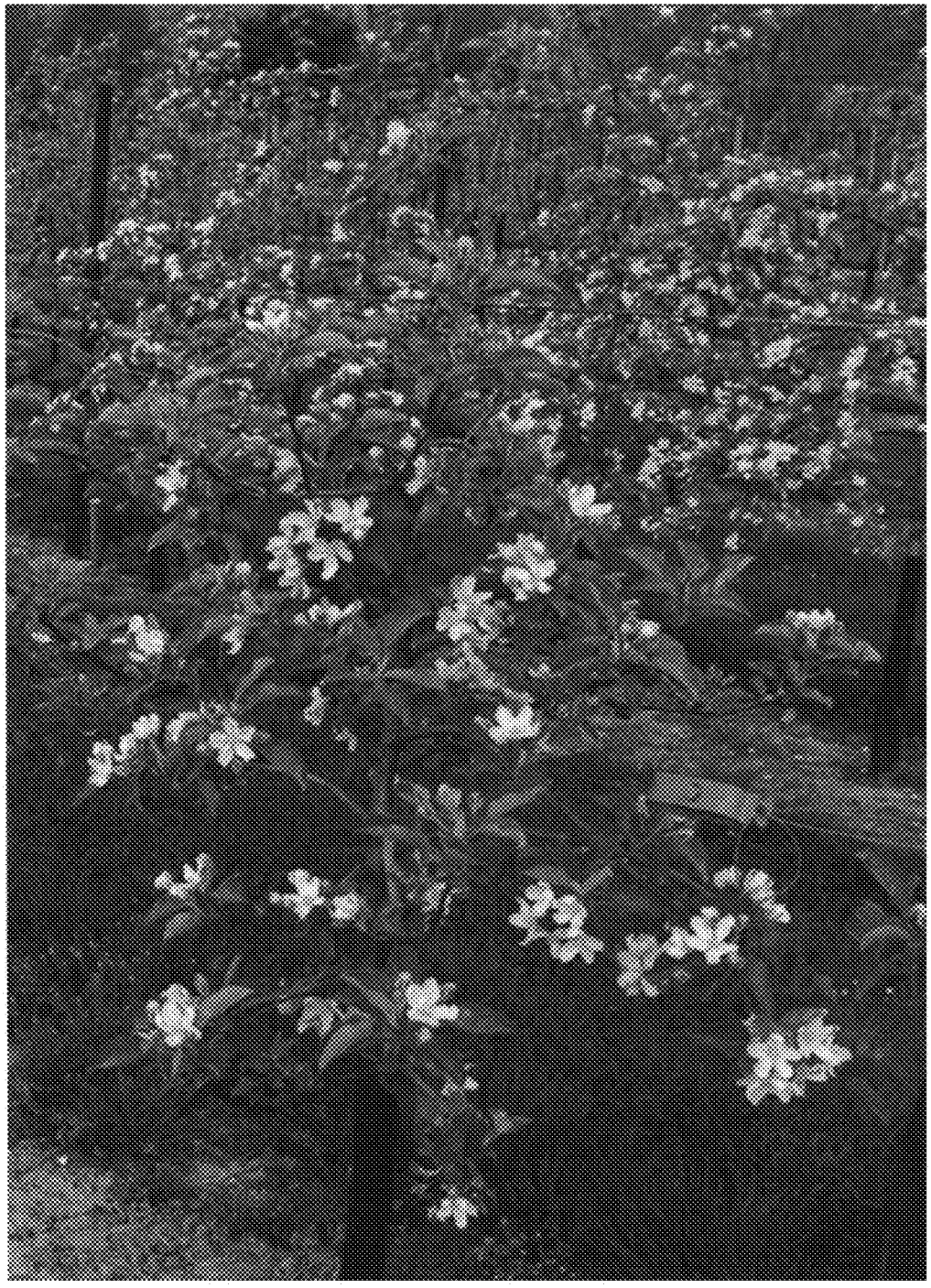
FIG. 3 illustrates flowers of apple tree variety 'ZOUK 32'.

The following description sets forth the distinctive characteristics of 'ZOUK 32'. The following botanical description of 'ZOUK 32' is based on observations of the originally identified tree, and asexually reproduced progeny, grown on 'M9 T337' rootstock in Sint-Truiden, Belgium. Referring more specifically to the details of the new and distinct variety of apple tree, unless otherwise stated, the following has been observed on trees that were four years of age growing on 'M9 T337' rootstock in Sint-Truiden, Belgium. Numbers provided are averages of data measured from the sampling trees.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from The R.H.S. Colour Chart of The Royal Horticultural Society of London (R.H.S.) (Sixth Edition, 2015).

Tree:

*Type.*—Ramified (comparable to 'Elstar' (U.S. Plant Pat. No. 6,450) and 'Golden Delicious' (unpatented)).

*Habit.*—Spreading (comparable to 'Bramley's Seedling' (unpatented) and 'Jonagold' (unpatented)).

*Time of beginning of flowering.*—Late to very late. In 2018 Sint-Truiden, Belgium, time of beginning of flowering was April 16$^{th}$.

*Time of fruit eating maturity.*—Medium (comparable to 'Elstar' (U.S. Plant Pat. No. 6,450), 'Gala' (U.S. Plant Pat. No. 3,637), and 'Honeycrisp' (U.S. Plant Pat. No. 7,197)). In 2018 in Sint-Truiden, Belgium, time of fruit eating maturity was September 6$^{th}$.

*Vigor.*—Medium to weak (comparable to 'Golden Delicious' (unpatented)).

*Overall shape.*—Spreading.

*Height.*—Approximately 2.50 m.

*Width.*—Approximately 1.45 m.

*Caliper.*—Approximately 40 mm at 50 mm above the graft union.

*Trunk bark texture.*—Smooth with raised, prominent lenticels.

*Trunk bark color.*—About greyed-green (RHS 197D).

*Patches or other markings.*—No prominent spots or scales evident.

*Primary branches.*—Stout; branches emerge at an angle of approximately 60 to approximately 90 degrees with branches higher in the tree emerging at approximately 60 degrees. Measured trees are grown to a central leader system. The typical and observed lateral branch length is 80 cm (first primary branch above graft union and arising from main stem).

*Branch color.*—One-year old branches are moderate brown (RHS 200C), while older branches are dark greyish yellowish brown (RHS N199C).

*Branch lenticels.*—Low to medium density, approximately 5 per square centimeter. Shape: Mostly oval. Color: Yellowish-white (RHS 156D). Size: Approximately 1.2 mm long by approximately 0.9 mm wide.

*Internodes.*—Average internode length is approximately 37.7 mm for a one-year old shoot.

*Lenticel density on shoot.*—5 lenticels per square centimeter for a one-year old shoot.

*Lenticel shape on shoot.*—Mostly oval with a few of the smaller ones having a round shape for a one-year-old shoot.

*Lenticel size on shoot.*—Approximately 1.2 mm long by approximately 0.7 mm wide for a one-year-old shoot.

*Bearing.*—Annual.

*Hardiness.*—European Zone 8 hardy (comparable to 'Royal Gala' (U.S. Plant Pat. No. 4,121) and 'Golden Delicious' (unpatented)).

*Disease resistance.*—Tolerance to apple scab caused by *Venturia inaequalis.*

Leaves:

*Texture.*—Upper leaf surface: Leathery. Lower leaf surface: Smooth.

*Sheen.*—Upper leaf surface: Glossy. Lower leaf surface: Not glossy.

*Margin.*—Dentate to slightly crenate.

*Tip surface.*—Acute.

*Stipules.*—2 present on 90% of leaves. Where present, opposite, slender.

*Leaf color.*—Upper leaf surface: Dark green (RHS 136A). Lower leaf surface: Light yellowish green (RHS 136D).

*Pubescence.*—Upper leaf surface: Absent to very fine. Lower leaf surface: Fine (light).

*Leaf blade length.*—113 mm.

*Leaf blade width.*—65 mm.

*Leaf blade attitude in relation to the shoot.*—Upwards.

*Petiole length.*—About 46 mm.

Flower:

General:

*Size.*—Between 44 and 52 mm in diameter, with an average of 48 mm.

*Shape.*—Ovoid to round.

*Color.*—Unopened bud: Strong purplish red (RHS 64C). Opened bud: White (RHS NN155D) with streaks of pale purplish pink (RHS 62D).

Petals:
*Numbers of petals per flower.*—5.
*Shape.*—Ovate. Base: Acuminate. Apex: Rounded.
*Arrangement.*—Separated but overlapping.
*Color.*—Upper petal surface: White (RHS NN155D) with streaks of pale purplish pink (RHS 62D). Lower petal surface: About white (RHS N155D) to moderate purplish pink (RHS 62B).

Sepals:
*Number.*—About 5 per flower.
*Color.*—Moderate yellow green (RHS 139C), tinged at the tip with about red-purple (RHS 59A).
*Arrangement.*—Arranged separately.

Pedicel/peduncle: Apples do not have branched inflorescences and hence do not have pedicels. The flower stalk of an apple is the peduncle.
*Length.*—25 mm.
*Diameter.*—1 mm.
*Color.*—Light yellow-green (RHS 145C).

Stamen:
*Number.*—Approximately 20 per flower, arranged in a row around the circumference of the receptacle.
*Filament color.*—Greenish white (RHS 155C).
*Anthers.*—About 20 per flower. Anther color: Pale yellow green (RHS 4D). Unopened anther color: About yellow (RHS 5D).
*Pollen color.*—Light greenish yellow (RHS 4B).
*Amount of pollen.*—Moderate.

Pollination requirements: Early flowering varieties, e.g., 'Braeburn' (unpatented), are preferred. Later flowering varieties, e.g., 'Granny Smith' (unpatented) or 'Golden Delicious' (unpatented), will overlap sufficiently in flowering to enable pollination.

Fragrance: Slight, apple-blossom-like.

Bloom season: In 2016 in Sint-Truiden, Belgium, full bloom was on the 1$^{st}$ of May.

Fruit:

General: Measurements are the average of 10 typical 'ZOUK 32' apples.
*Eye.*—Erect divergent. Diameter: Between 10 and 12 mm.
*Sepal color.*—Moderate yellow green (RHS 139C) with downy yellowish white (RHS 158C) hairs.

Size: Medium to large.
*Length.*—Approximately 75.3 mm.
*Width.*—Approximately 72 mm.

Shape: Globose-conical, slightly elongated; very slight lobes observed at calyx end. The calyx is slightly open (0.5 mm to 1.5 mm—with an average of 1.0 mm for ten fruit).
*Cavity.*—Width: Approximately 28.6 mm. Depth: Approximately 10 mm.
*Basin.*—Shape: Concave. Width: Approximately 24.4 mm. Depth: Approximately 12 mm.

Fruit stem:
*Length.*—Approximately 20.5 mm.
*Diameter.*—Approximately 2.5 mm.
*Color.*—Yellow-green (RHS 144B).

Locules: 5 slightly open locules with seeds free of the carpel wall at maturity.

Fruit skin:
*Tendency to crack.*—Absent.
*Thickness.*—Medium.
*Surface texture.*—Glossy.
*Lenticels.*—Present, approximately 0.5 to approximately 1.0 mm in diameter, generally yellow-white in color (RHS 158A), and at an average density of about 5 lenticels/cm$^2$.
*Color.*—General color effect: Vivid reddish orange (RHS 42A). Ground color: At maturity, about brilliant yellow (RHS 14C). Over color: About red (RHS 42A).
*Russetting.*—Slight amount inside stem cavity.
*Bloom of the skin.*—Moderate.

Fruit flesh:
*Flavor.*—Mild, with a good balance between sweet and sour.
*Brix.*—Average approximately 15 Brix.
*Juiciness.*—Very juicy.
*Color.*—Pale yellow (RHS 8D).
*Aroma.*—Apple-like, moderate in intensity.
*Firmness.*—Firm.

Core: While the calyx can be open in about 70 percent of fruit, the calyx tube is closed and the core lines are defined.
*Shape.*—Round to slightly elongate.
*Number of bundles.*—Approximately 10 per fruit.

Seed:
*Number.*—About 1 to 2 seeds per cell.
*Shape.*—Acute in shape.
*Color.*—Moderate brown (RHS 165A).

Fruit production: First picking date in the 2017 season at Sint-Truiden, Belgium, was about the 12$^{th}$ of September.

Storage: Fruit remains fresh at room temperature (approximately 20° C.) for approximately 7 days, and can be stored up to approximately six months in cold storage (about 1° C. or about 34° F.).

Usage: Fresh eating.

COMPARISONS TO PARENTAL AND SIMILAR VARIETIES

The 'ZOUK 32' apple tree variety is distinguished from seed parent 'Rubinstep' by the following unique combination of characteristics: fruit of 'ZOUK 32' has a smoother skin and is less flat in shape than fruit of 'Rubinstep'; and fruit of 'ZOUK 32' has more of a pink-red color than the more orange-red color of fruit of 'Rubinstep'.

The 'ZOUK 32' apple tree variety is distinguished from pollen parent 'Nicoter' by the following unique combination of characteristics: 'ZOUK 32' matures approximately three weeks earlier (beginning of September) than does 'Nicoter' (3$^{rd}$ week of September); 'ZOUK 32' is higher yielding than 'Nicoter'; 'ZOUK 32' is less sensitive to frost than is 'Nicoter'; and fruit of 'ZOUK 32' is more flat-globose in shape, while fruit of 'Nicoter' is short conical-globose in shape.

Table 1 below compares some of the characteristics of the 'ZOUK 32' apple tree variety with the similar apple tree varieties, 'Gala 2013' (U.S. Plant Pat. No. 27,978), 'BL-14' (U.S. Plant Pat. No. 27,867), and 'Gala Schnico Red' (U.S. Plant Pat. No. 27,577).

TABLE 1

| Characteristic | 'Gala 2013' | 'BL-14' | 'Gala Schnico Red' | 'ZOUK 32' |
|---|---|---|---|---|
| Branch color | Grey (RHS 201C) | Grey-brown group 199A (scaffold branches) | Greyish brown | Dark greyish yellowish brown (RHS N199C) |
| Number of lenticels on one year old shoot | 6 to 8 per square centimeter | 14 per running cm of growth | N/A | 5 per square centimeter |
| Hardiness | European Zone 6 | USDA Zone 6b | European Zone 8 | European Zone 8 |
| Petiole length | 34 mm | 28.5 mm | 30 mm | 46 mm |
| Petal color | Colour of upper surface, white (RHS NN155C) with reddish shades red purple (RHS 64C); colour of lower surface, white (RHS NN155B) | Background color is white (20%), overcolor both upper and lower surfaces is variable in the red-purple group 62D and 63A | Color (upper and lower surfaces) = white (CPVO/UPOV Nr.19, Note 1) and light pink (upper) (CPVO/UPOV Nr.19, Note 3); white (under) (CPVO/UPOV Nr.19, Note 1) | Upper petal surface: White (RHS NN155D) with streaks of pale purplish pink (RHS 62D). Lower petal surface: About white (RHS N155D) to moderate purplish pink (RHS 62B) |
| Fruit shape | Globose | Round conical | Conical | Globose-conical, slightly elongated |
| Fruit skin color at harvest | Background colour, red (RHS 53A); pattern of over-colour, solid flush; over colour of skin, red purple (RHS 60A) | Wash under color from the red group 47A, stripe over color from the red group 46A | The hue of over colour with bloom removed is purple red (CPVO/UPOV Nr.37, Note 4) | General color effect: Vivid reddish orange (RHS 42A). Ground color: At maturity, about brilliant yellow (RHS 14C). Over color: About red (RHS 42A) |
| Fruit flesh firmness | Medium to firm | Crisp, firm | 6,5-7 kg/cm2 (medium) | Firm |
| Seed shape | Oval elongated | Mostly obtuse with occasional acute | Elliptic | Acute |
| Seed color | Brown greyed-orange (RHS 166A) | From the greyed-orange group 177A | Red brown | Moderate brown (RHS 165A) |

What is claimed is:

1. A new and distinct variety of apple tree named 'ZOUK 32' as shown and described herein.

* * * * *